(12) United States Patent
Høy et al.

(10) Patent No.: US 6,787,529 B2
(45) Date of Patent: Sep. 7, 2004

(54) TOPICAL COMPOSITION

(75) Inventors: Gert Høy, Jyllinge (DK); Erik Johannes Didriksen, Ballerup (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 0 days.

(21) Appl. No.: 09/984,072

(22) Filed: Oct. 26, 2001

(65) Prior Publication Data

US 2002/0111336 A1 Aug. 15, 2002

Related U.S. Application Data

(60) Provisional application No. 60/243,471, filed on Oct. 27, 2000.

(51) Int. Cl.$^7$ .................. A61K 31/59; A61K 31/56; A61K 31/41; A61K 31/44

(52) U.S. Cl. .................. 514/167; 514/178; 514/336; 514/383; 514/169; 424/484; 424/485; 424/486; 424/487; 424/488

(58) Field of Search ................... 514/167, 178, 514/336, 383, 169; 424/484–488

(56) References Cited

U.S. PATENT DOCUMENTS

| | | | |
|---|---|---|---|
| 4,569,935 A | * | 2/1986 | Rosenberg et al. |
| 4,610,978 A | | 9/1986 | Dikstein et al. |
| 5,185,150 A | | 2/1993 | DeLuca et al. |
| 5,827,520 A | * | 10/1998 | de Salvert |

FOREIGN PATENT DOCUMENTS

| | | |
|---|---|---|
| EP | 0 471 872 A1 | 2/1992 |
| WO | WO94/14453 | 7/1994 |
| WO | WO00/64450 | 11/2000 |

OTHER PUBLICATIONS

Ruzick et al., British Journal of Dermatology 1998; 139: 254–258.*

Gennaro, Remington's Pharmaceutical Sciences, 18th ed., p. 1310–1311.*

* cited by examiner

*Primary Examiner*—San Ming Hui
(74) *Attorney, Agent, or Firm*—Birch, Stewart, Kolasch & Birch, LLP

(57) ABSTRACT

The present invention relates to a pharmaceutical gel composition for application on skin, said composition comprising at least one vitamin D or vitamin D analogue and at least one corticosteroid as well as a viscosity-increasing excipient.

23 Claims, No Drawings

TOPICAL COMPOSITION

This application claims the benefit of Provisional Application No. 60/243,471 filed Oct. 27, 2000.

FIELD OF THE INVENTION

The present invention concerns topical compositions for application on skin which contain at least one vitamin D or vitamin D analogue and at least one corticosteroid.

BACKGROUND OF THE INVENTION

In the treatment of a number of conditions using dermal application, e.g. in the treatment of psoriasis, it is often indicated to employ a combination treatment incorporating two or even more different pharmacologically active compounds. Thus, in the treatment of e.g. psoriasis, it is known to use a combination treatment involving a steroid compound, such as a corticosteroid compound, and a vitamin D analogue such as calcipotriol, and where each of the active compounds are formulated in separate preparations due to the instability of corticosteroids at alkaline pH values and of vitamin D analogues at acid pH values.

Consequently, physicians have had to resort to letting patients under this type of two-component regimen perform sequential application of two creams/ointments, each containing one of the compounds formulated at its maximum stability pH. This may lead to incompatibility of the preparations so that patients must, e.g., apply one cream/ointment in the morning and the other in the evening. Needless to say, patient compliance as well as correct administration dosage is a problem under such circumstances. Richards, H. L. et al. report in *J Am Acad Dermatol* October 1999; 41(4):581-3 on a study of patients with psoriasis and their compliance with medication. They report that poor compliance with treatment advice in chronic conditions, such as psoriasis, represents a major challenge to health care professionals: Thirty-nine percent of participants reported that they did not comply with the treatment regimen recommended. The noncompliant group had a higher self-rated severity of psoriasis, were younger, and had a younger age at onset than those who were compliant. The noncompliant group reported that psoriasis had a greater impact on daily life.

WO 00/64450 describes a pharmaceutical composition for dermal use comprising a combination of a vitamin D analogue and a corticosteroid, which composition alleviates the inconveniences of a two-component or multi-component regimen for the treatment of psoriasis and related skin diseases. This composition, however, tends to be rather oily and to leave, on application, a greasy film of non-absorbed excipients on the skin.

SUMMARY OF THE INVENTION

It is therefore the object of the present invention to provide a composition comprising both active components in a formulation exhibiting improved skin absorption (and less oily appearance) and ease of application, both qualities leading to improved patient compliance.

Accordingly, the present invention relates to a pharmaceutical gel composition for application on skin, said composition comprising at least one vitamin D or vitamin D analogue and at least one corticosteroid, said composition further comprising a viscosity-increasing excipient in an amount resulting in a viscosity which, on the one hand, is sufficient to substantially prevent the corticosteroid from sedimenting during application and storage of the composition and, on the other hand, is sufficient to facilitate an even distribution of the composition on an affected skin area, The gel composition of the invention has been found to be particularly favourable for application on the scalp due to the ease with which it may be applied and to the considerably less oily appearance which makes the composition more acceptable to patients suffering from psoriasis of the scalp.

In another aspect, the invention relates to the use of a gel composition as defined above for the manufacture of a medicament for the topical treatment of psoriasis and related conditions, e.g. sebo-psoriasis of the scalp, in humans.

DETAILED DESCRIPTION OF THE INVENTION

In the present context, the term "sufficient", when used in connection with viscosity, is understood to indicate a viscosity which, on the one hand, is sufficiently high to ensure that the corticosteroid (which is present in the composition in the form of dispersed particles) does not sediment from the composition which would, of course, result in an uneven application of the corticosteroid over the affected area. On the other hand, the viscosity of the application should be sufficiently low to enable the patient to readily remove the required dose of the composition from the container in which it is available (e.g. a tube or the like) and apply it evenly over the affected area to ensure an even dosing of the active components.

For application of the present composition on the scalp, it is particularly important to ensure that the viscosity is sufficiently high to substantially prevent "leakage" of the composition from the area where it is applied to other areas, in particular the face. It is equally important that the composition is readily applied on an area of skin covered by hair to ensure correct dosing of the active components.

In practical terms, this means that the viscosity should preferably be in the range of from about 5 mPa.s to about 500 mPa.s, in particular from about 10 mPa.s to about 250 mPa.s, such as from about 20 mPa.s to about 100 mPa.s. The viscosity may suitably be determined by the cup/rotor method involving an NV1 device on a Haake VT 550 viscosimeter at 700 $s^{-1}$ and 20° C.

In a currently favoured embodiment, a suitable viscosity of the composition may be obtained by including a thixotropic gelling agent as the viscosity-increasing excipient such that the composition, on standing, is in the form of a gel. A thixotropic agent has the advantage of being readily applied while, on standing, such as after application, the viscosity increases so that the composition will typically not leak from affected areas of skin on which it is applied to unaffected areas. An example of a suitable thixotropic gelling agent is hydrogenated castor oil.

In an alternative embodiment, the viscosity-increasing excipient may be selected from a wax, e.g. Cera Alba (white wax) or Cera Flava (yellow wax), polyethylene or a microcrystalline wax such as Esma-P®.

When the composition is an emulsion, it may be a water-in-oil or oil-in-water emulsion comprising a suitable emulsifier which may, for instance, be selected from polyoxyethylene cetyl ether, polyoxyethylene stearyl ether or polyoxyethylene oleyl ether, or polyethyleneglycol dipolyhydroxystearate.

In order to circumvent the problem of instability of certain vitamin D analogues in an acid environment (they have a maximum stability at pH values above about 8) and instability of corticosteroids in an alkaline environment (they have a maximum stability at a pH of about 4–6), it is furthermore preferred that the composition is substantially non-aqueous. The term "substantially non-aqueous" is intended to indicate that the composition has a water content below about 5%, preferably below about 2%, such as below about 1.5%.

Consequently, the composition preferably comprises at least one substantially non-aqueous solvent selected for its ability to dissolve or solubilise the vitamin D analogue. The solvent may suitably be selected from the group consisting of:

(i) compounds of the general formula $R^3(OCH_2C(R^1)H)_xOR^2$ (I) wherein x is in the range of 2–60, $R^1$ in each of the x units independently is H or $CH_3$, $R^2$ is straight chain or branched $C_{1-20}$alkyl or benzoyl, and $R^3$ is H or phenylcarbonyloxy;

(ii) di-(straight or branched)-$C_{4-10}$ alkyl esters of $C_4$–$C_8$ dicarboxylic acids;

(iii) straight or branched $C_{12-18}$-alkyl benzoates;

(iv) straight or branched $C_{2-4}$-alkyl esters of straight or branched $C_{10-18}$-alkanoic or-alkenoic acids;

(v) propylenglycol diesters with $C_{8-14}$-alkanoic acids; and (vi) branched primary $C_{18-24}$ alkanols.

It has been found that in such combination compositions containing a solvent selected from one of the group indicated above and in a substantially non-aqueous environment, the active components can co-exist without degradation, despite their different pH/stability profiles. The tendencies of the active compounds to affect one another with regard to pH is minimised or eliminated.

In the general formula (I) defined above, it is preferred that the factor x (which designates the number of the units within the parentheses) is in the range 4–50, more preferably 4–40, in particular 4–30, especially 5–25, more especially 10–20, such as about 15. It is further preferred that $R^1$ is $CH_3$.

It is preferred that the solvent is selected from compounds of the general formula $H(OCH_2C(R^1)H)_xOR^2$ (II) where $R^1$, x, and $R^2$ are as defined above, and mixtures thereof.

As non-limiting specific examples of the types (i)–(vi) of the solvent defined above may be mentioned the following, including trade names:

Arlamol E (polyoxyethylene(15) stearyl ether);

Arlamol DoA (diisooctyl ester of adipic acid);

Arlasolve 200 (Polyoxyethylene-20-isohexadecyl ether);

Eutanol G (2-octyldodecanol);

Finsolv (Isostearyl benzoate);

Finsolv P (polyoxypropylene-15-stearyl ether benzoate);

Isopropylesters of straight or branched $C_{10}$–$C_{18}$ alkanoic or alkenoic acids such as isopropyl myristate, isopropyl palmitate, isopropyl isostearate, isopropyl linolate and isopropyl monooleate;

Miglyol 840 (Propylene glycol diester of caprylic and caprinic acid);

DPPG (propylene glycol dipelagonate);

Procetyl AWS $(CH_3(CH_2)_{14}CH_2(OCH(CH_3)CH_2)_5$—$(OCH_2)_{20}OH)$.

In the present context, the term "vitamin D analogue" is intended to indicate a synthetic compound comprising a vitamin D scaffold with sidechain modifications and/or modifications of the vitamin D scaffold itself. The term is not intended to include naturally occurring vitamin D derivatives such as metabolites.

The vitamin D analogue included in the present composition is preferably a compound selected from the group consisting of seocalcitol; calcipotriol; calcitriol; tacalcitol, maxacalcitol; paricalcitol; falecalcitriol; 1α,24S-dihydroxy-vitamin D2; and 1(S),3(R)-dihydroxy-20(R)-[((3-(2-hydroxy-2-propyl)-phenyl)-methoxy)-methyl]-9,10-seco-pregna-5(Z),7(E),10(19)-triene, as well as mixtures thereof.

More preferred are vitamin D analogues selected from the group consisting of calcipotriol, calcitriol, tacalcitol, maxacalcitol, and 1(S),3(R)-dihydroxy-20(R)-[((3-(2-hydroxy-2-propyl)-phenyl)-meth oxy)-methyl]-9,10-seco-pregna-5(Z),7(E),10(19)-triene as well as mixtures thereof. Synthetic vitamin D analogues are more preferred in the compositions according to the invention than naturally occurring vitamin D's or vitamin D derivatives, since the therapeutic effects of the latter may be less selective for the treatment of skin diseases, such as psoriasis.

Further non-limiting examples of vitamin D analogues are:

alphacalcidol;

1α-hydroxy-vitamin D2;

1α-hydroxy-vitamin D5;

1(S),3(R)-Dihydroxy-20(R)-(5-ethyl-5-hydroxy-1-heptyl)-9,10-secopregna-5(Z),7(E),10(19)-triene;

1(S),3(R)-Dihydroxy-20(R)-(6-hydroxy-6-methyl-1-heptyl)-9,10-secopregna-5(2), 7(E),10(19)-triene;

1(S),3(R)-Dihydroxy-20(R)-(6-hydroxy-6-methylhept-1(E)-ene-1-yl-9,10)-secopregna-5(Z),7(E),10(19)-triene;

1(S),3(R)-Dihydroxy-20(R)-(6-ethyl-6-hydroxy-1-octyl)-9,10)-secopregna-5(Z),7(E),10(19)-triene;

1(S),3(R)-Dihydroxy-20(R)-(7-hydroxy-7-methyl-1-octyl)-9,10)-secopregna-5(2),7(E),10(19)-triene;

1(S),3(R)-Dihydroxy-20(R)-(7-hydroxy-7-methyloct-1(E)-en-1-yl-9,10)-secopregna-5(Z),7(E),10(19)-triene;

1(S),3(R)-Dihydroxy-20(R)-(6'-methyl-1'-heptyl)-9,10-secopregna-5(Z), 7(E),10(19)-triene;

1(S),3(R)-Dihydroxy-20(S)-(5'-hydroxy-5'-methyl-1'-hexyloxy)-9,10-secopregna-5(Z),7(E),10(19)-triene;

1(S),3(R)-Dihydroxy-20(R)-(4'-hydroxy-4'ethyl-1'-hexyloxy)-9,10-seco-pregna-5(Z),7(E),10(19)-triene;

1(S),3(R)-Dihydroxy-20(R)-(6'-hydroxy-1'-hexyloxy-9,10-seco-pregna-5(Z), 7(E),10(19)-triene;

1(S),3(R)-Dihydroxy-20(R)-(5'-hydroxy-5'-ethyl-1'-heptyloxy)-9,10-seco-pregna-5(Z),7(E),10(19-triene;

1(S) 3(R)-Dihydroxy-20(R)-(5'-hydroxy-5'-methy-1'-hexyloxy)-9,10-seco-pregna-5(Z),7(E),10(19)-triene;

1(S),3(R)-Dihydroxy-20(R)-(5'-methyl-1'-hexyloxy)-9,10-seco-pregna-5(Z),7(E),10(19-triene;

1(S),3(R)-Dihydroxy-20(R)-(4'-hydroxy-4'-(1"-propyl)-1'-heptyloxy)-9,10-seco-pregna (Z),7(E),10(19)-triene;

1(S),3(R)-Dihydroxy-20(R)-(4'-hydroxy-4'-(1"-propyl)-1-heptyloxy)-9,10-seco-pregna (Z),7(E),10(19)-triene;

1(S),3(R)-Dihydroxy-20(R)-(4'-hydroxy-4'-methyl)-1'-pentyloxy)-9,10-seco-pregna-5(Z),7(E),10(19)-triene;

1(S),3(R)-Dihydroxy-20(R)-(3'-hydroxy-3'-methyl-1'-butyloxy)-9,10-seco-pregna-5(Z),7(E),10(19)-triene;

1(S),3(R)-Dihydroxy-20(S)-(4-hydroxy-4-methyl-1-pentyl)-9,10-secopregna-(5(Z),7(E),10(19)-triene;

1(S),3(R)-Dihydroxy-20(S)-(5-ethyl-5-hydroxy-1-hept-yl)-9,10-secopregna-5(Z),7(E),10(19)-triene;

1(S),3(R)-Dihydroxy-20(S)-(5-ethyl-5-hydroxy-hept 1(E)-en-1-yl),9,10-secopregna-5(2),7(E),10(19)-triene;

1(S),3(R)-Dihydroxy-20(5'-hydroxy-5methyl-hexa-1'(E)-dien-1'-yl),9,10-secopregna-5(2),7(E),10(19)-triene;

1(S),3(R)-Dihydroxy-20-(5'ethyl-5'-hydroxy-hepta-1'(E),3'(E)-dien-1'-yl)-9,10-secopregna-5(Z),7(E),10(19)-triene;

1(S),3(R)-Dihydroxy-20-(6'-hydroxy-hexa-1'(E),3'(E)-dien-1'-yl)-9,10-seco-pregna (Z),7(E),10(19)-triene;

1(S),3(R)-Dihydroxy-20-(5'-cyclopropyl-5'-hydroxy-penta-1'(E),3'(E)-dien-1'-yl)-9,10-secopregna-5(Z)-7(E),10,19-triene (5'(R) and 5'(S) isomers);

1(S),3(R)-Dihydroxy-20-(6'-hydroxy-6'-methyl-hepta-1'(E),3"(E)-dien-1'-yl)-9,10-secopregna-5(Z),7(E),10(19)-triene;

1(S),3(R)-Dihydroxy-20(R)-(3-(2-hydroxy-2-pentyl)-phenylmethoxy)-9,10-seco-pregna-5(Z),7(E),10(19)-triene;

1(S),3(R)-Dihydroxy-20(R)-(3-(3-hydroxy-3-propyl)-phenylmethoxy)-9,10-seco-pregna-5(Z),7(E),10(19)-triene;

1(S),3(R)-Dihydroxy-20(R)-(4-hydroxy-4-methyl-1-pentyloxymethyl)-9,10-seco-pregna-5(Z),7(E),10(19)-triene;

1(S),3(R)-Dihydroxy-20(R)-(4-hydroxy-4-methyl-1-pent-2-ynyloxymethyl)-9,10-seco-pregna-5(Z),7(E),10(19)-triene;

1(S),3(R)-Dihydroxy-20(R)-(4-hydroxy-4-trifluoromethyl-5,5,5-trifluoro-1-pent-2ynyloxymethyl)-9,10-seco-pregna-5(Z),7(E),10(19)-triene;

1(S),3(R)-Dihydroxy-20(R)-[3-(2-hydroxy-2-propyl)-phenoxymethyl]-9,10-seco-pregna-5(Z),7(E),10(19)-triene;

1(S),3(R)-Dihydroxy-20(R)-[((3-(2-hydroxy-2-propyl)-phenyl)-methoxy)-methyl]-9,10-seco-pregna-5(Z),7(E),10(19)-triene;

1(S),3(R)-Dihydroxy-20(R)-[((3-(2-hydroxy-2-propyl)-5-methylphenyl)-methoxy]-9,10-seco-pregna-5(Z),7(E),10(19)-triene;

1(S),3(R)-Dihydroxy-20(R)-[((3-(2-hydroxy-2-propyl)-5-methoxyphenyl)-methoxy)-methyl]-9,10-seco-pregna-5(Z),7(E),10(19)-triene;

1(S),3(R)-Dihydroxy-20(R)-(3-hydroxy-3-ethyl-1-pentylthiomethyl)-9,10-seco-pregna-5(Z),7(E),10(19)-triene;

1(S),3(R)-Dihydroxy-20(R)-(3-hydroxy-3-ethyl-1-pentylsulphonylmethyl)-9,10-seco-pregna-5(Z),7(E),10(19)-triene;

1(S),3(R)-Dihydroxy-20(R)-(3-((1-hydroxy-1-methyl)ethyl)phenylthiomethyl)-9,10-seco-pregna-5(Z),7(E),10(19)-triene;

1(S),3(R)-Dihydroxy-20(R)-(3,3-difluoro-4-hydroxy-4-methyl-1-pentyloxymethyl)-9,10-seco-pregna-5(Z)-7(E),10(19)-triene;

1(S),3(R)-Dihydroxy-20(R)-(6'-ethyl-6'-hydroxy-oct-1'-yn-1'-yl)-9,10-seco-pregna-5(Z),7(E)-10(19)-triene;

1(S),3(R)-Dihydroxy-20(R)-(7'-ethyl-7'-hydroxy-non-1'-yn-1'-yl)-9,10-seco-pregna-5(Z),7(E),10(19)-triene;

1(S),3(R)-Dihydroxy-20(R)-(1,5-dihydroxy-5-ethyl-2-heptyn-1-yl)-9,10-seco-pregna-5(Z),7(E)-10(19)-triene; isomer A;

1(S),3(R)-Dihydroxy-20(R)-(5-ethyl-5-hydroxy-1-methoxy-2-heptyn-1-yl)-9,10-seco-pregna-5(Z),7(E)-10(19)-triene; isomer A;

1(S),3(R)-Dihydroxy-20(R)-(1-ethoxy-5-ethyl-5-hydroxy-2-heptyn-1-yl)-9,10-seco-pregna-5(Z),7(E)-10(19)-triene; isomer A;

1(S),3(R)-Dihydroxy-20(R)-(1-methoxy-4-hydroxy-4-ethyl-2-hexyn-1-yl)-9,10-seco-prega-5(Z),7(E)-10(19)-triene; isomer A;

1(S),3(R)-Dihydroxy-20(R)-(1-ethoxy-4-hydroxy-4-ethyl-2-hexyn-1-yl)-9,10-seco-pregna-5(Z),7(E)-10(19)-triene; isomer A;

1(S),3(R)-Dihydroxy-20-(4-ethyl-4-hydroxy-1-hexyn-1-yl)-9,10-seco-pregna-5(Z),7(E)-10(19) 17(20)(Z)-tetraene;

1(S),3(R)-Dihydroxy-20-(5-ethyl-5-hydroxy-1-heptyn-1-yl)-9,10-seco-pregna-5(Z),7(E)-10(19),17(20)(Z)-tetraene;

1(S),3(R)-Dihydroxy-20-(6-ethyl-6-hydroxy-1-octyn-1-yl)-9,10-seco-pregna-5(Z),7(E),10(19),17(20)(Z)-tetraene;

1(S),3(R)-Dihydroxy-20(R)-(5-ethyl-4,4-difluoro-5-hydroxy-heptyloxy)-9,10-seco-pregna-5(Z),7(E),10(19)-triene;

1(S),3(R)-Dihydroxy-20(R)-(4,4-dichloro-5-hydroxy-5-methyl-hexyloxy)-9,10-seco-pregna-5(Z),7(E)-10(19)-triene;

1(S),3(R)-Dihydroxy-20(R)-(4,4-difluoro-5-hydroxy-5-methyl-hexyloxy)-9,10-seco-pregna-5(Z),7(E)-10(19)-triene;

1(S),3(R)-Dihydroxy-20(R)-(4-fluoro-4-methyl-pentyloxy)-9,10-seco-pregna-5(Z),7(E),10(19)-triene;

1(S),3(R)-Dihydroxy-20(R)-(4-ethyl-4-fluoro-hexyloxy)-9,10-seco-pregna-5(Z),7(E),10(19)-triene;

1(S),3(R)-Dihydroxy-20(R)-(5-fluoro-5-methyl-hexyloxy)-9,10-seco-pregna-5(Z),7(E),10(19)-triene;

1(S),3(R),20(S)-Trihydroxy-20-(4-ethyl-4-hydroxy-1-hexyl)-9,10-secopregna-5(Z),7(E),10(19)-triene;

1(S),3(R)-Dihydroxy-20(S)-methoxy-20-(4-ethyl-4-hydroxy-1-hexyl)-9,10-secopregna-5(Z),7(E),10(19)-triene;

1(S),3(R)-Dihydroxy-20(S)-ethoxy-20-(4-ethyl-4-hydroxy-1-hexyl)-9,10-secopregna-5(Z),7(E),10(19)-triene;

1(S),3(R)-Dihydroxy-20(S)-[3-(2-hydroxy-2-methyl-1-propoxy)-prop-1E-en-1-yl]-9,10-seco-pregna-5(Z),7(E),10(19)-triene;

1(S),3(R)-Dihydroxy-20(R)-(4-ethyl-4-hydroxy-1-hexylthio)-9,10-seco-pregna-5(Z),7(E),10(19)-triene;

1(S),3(R)-Dihydroxy-20(R)-[5-methyl-5-hydroxy-1-hexylthio]-9,10-seco-pregna-5(Z),7(E),10(19)-triene;

1(S),3(R)-Dihydroxy-20(R)-[3-(1-methyl-1-hydroxyethyl)benzylthio]-9,10-seco-pregna-5(Z),7E),10(19)-triene;

1(5),3(R)-Dihydroxy-20(R)-(3-methyl-3-hydroxy-1-butylthio)-9,10-seco-pregna-5(Z)-7(E),10(19)-triene;

1(5),3(R)-Dihydroxy-20(R)-(5-ethyl-5-hydroxy-hept-1(E)-en-3-yn-1-yl)-9,10-seco-pregna-5(Z),7(E),10(19)-triene;

24-oxo-1(S),3(R),25-Trihydroxy-20(S)-9,10-seco-cholesta-5(Z),7(E),10,19-triene;

1(S),3(R)-Dihydroxy-20(R)-(3-oxo-4-hydroxy-4-ethyl-1-hexyloxy)-9,10-seco-pregna-5(Z),7(E),10(19)-triene;

1(S),3(R)-Dihydroxy-20-methyl-18-(5-ethyl-4-hydroxy-hexyloxy)-9,10-seco-pregna-5(Z),7(E),10(19)-triene;

1(S),3(R)-Dihydroxy-20-methyl-18-(4-ethyl-4-hydroxy-hexyloxy)-9,10-seco-pregna-5(Z),7(E),10(19)-triene;

1(S),3(R)-Dihydroxy-20-methyl-18-(4-ethyl-4-hydroxy-hex-2-ynyloxy)-9,10-seco-pregna-5(Z),7(E),10(19)-triene;

1(S),3(R)-Dihydroxy-20-methyl-18-(4-hydroxy-4-methylpentyloxy)-9,10-seco-pregna-5(Z),7(E),10(19)-triene;

1(S),3(R)-Dihydroxy-20-methyl-18-(4-hydroxy-4-methylpent)-2-yn-1-yloxy)-9,10-seco-pregna-5(Z),17(E),10(19)-triene;

1(S),3(R)-Dihydroxy-20-methyl-18-(3,1-hydroxy-1-methylethyl)phenylmethyloxy)-9,10-seco-pregna-5(Z),7(E),10(19)-triene;

1(S),3(R)-Dihydroxy-20(R)-(1-methoxy-4-hydroxy-4-methyl-1-pentyl)-9,10-seco-pregna-5(Z),7(E),10(19)-triene; isomer A;

1(S),3(R)-Dihydroxy-20(R)-(1-ethoxy-4-hydroxy-4-methyl-1-pentyl)-9,10-seco-pregna-5(Z),7(E),10(19)-triene; isomer A;

1(S),3(R),25-Trihydroxy-(20(S)-9,10-seco-cholesta-5(Z),7(E),10(19),23(E)-tetraene 1(S),3(R)-Dihydroxy-(20(S)-(6'-hydroxy-6'-methyl-4'(E)-hepten-1'yl)-9,10-seco-pregna-5(Z),7(E),10(19)-triene;

1(S),3(R),22(S),25-Tetrahydroxy-20(R),9,10-seco-cholesta-5(Z),7(E),10(19),23(E)-tetraene 22(S)-Ethoxy-1(S)-3(R),25-trihydroxy-10(R)-,9,10-seco-cholesta-5(Z),7(E),10(1,23(E)-tetraene 1(S),3(R)-Dihydroxy-20(S)-(3-(1-hydroxy-1-methylethyl)phenoxymethyl)-9,10-secopregna-5(Z),7(E),10(19),16-tetraene or the corresponding 20(R) isomer;

1(S),3(R)-Dihydroxy-20(S)-(3-(1-hydroxy-1-methylethyl)phenylthiomethyl)-9,10-secopregna-5(Z),7(E),10(19),16-tetraene or the corresponding 20(R) isomer;

1(S),3(R)-Dihydroxy-20(S)-(4-hydroxy-4-methylpent-1-yl)-9,10-secopregna-5(Z),7(E),10(19),16-tetraene;

1(S),3(R)-Dihydroxy-20(R)-(5-ethyl-5-hydroxyhept-1-yl)-9,10-secopregna-5(Z),7(E),10(19),16-tetraene or the corresponding 20(S) isomer;

1(S),3(R)-Dihydroxy-20(R)-(5-ethyl-5-hydroxyhepta-1(E),3(E)-dien-1-yl)-9,10-secopregna-5(Z),7(E),10(19),16-tetraene or the corresponding 20(S) isomer;

1(S),3(R)-Dihydroxy-20(R)-(3-cyclopropyl-3-hydroxyprop-1(E)-en-1-yl)-9,10-secopregna-5(Z),7(E),10(19),16-tetraene (24(S) isomer) or the corresponding 24(R) isomer; and 1(S),3(R)-Dihydroxy-20(1,2-dihydroxy-5-ethyl-2-heptyn-1-yl)-9,10-secopregna-5(Z),7(E),10(19),17(20)Z-tetraene, both 22-isomers.

The corticosteroid may be a group I, II, III or IV topical steroid. The corticosteroid is preferably selected from the group consisting of Betamethasone (9-fluoro-11,17,21-trihydroxy-16-methylpregna-1,4-diene-3,20-dione) and esters thereof such as the 21-acetate, 17-adamantoate, 17-benzoate, 17-valerate, and 17,21-dipropionate; Alclomethasone and esters thereof such as the dipropionate; Clobetasole and esters thereof such as the propionate; Clobetasone and esters thereof such as the 17-butyrate; Desoximetasone; Diflucortolon and esters thereof, Diflorasone and esters thereof such as the diacetate; Fluocinonid; Flumetasone and esters thereof such as the pivalate; Fluocinolon and ethers and esters thereof such as the acetonide; Fluticasone and esters thereof such as the propionate; Flu- prednidene and esters thereof such as the acetate; Halcinonide; Hydrocortisone and esters thereof such as the -17-butyrate; Mometasone and esters thereof such as the furoate; and Triamcinolon and ethers and esters thereof such as the acetonide; as well as mixtures thereof. More preferred examples of the corticosteroids are Betamethasone or esters thereof such as the 17-valerate or the 17,21-dipropionate, Clobetasole or esters thereof such as the propionate, Triamcinolon or ethers and/or thereof such as the acetonide or the acetonide-21-N-benzoyl-2-methyl-β-alaninate or the acetonide-21-(3,3-dimethylbutyrate), or Hydrocortisone or esters thereof such as the 17-butyrate.

The composition of the present invention may be prepared in accordance with methods well known to the person skilled in the field of pharmaceutical formulation. Thus, the non-aqueous compositions may be prepared by incorporating the components into a well known ointment or lotion base excipient such as liquid paraffin or Plastibase™ (a base prepared from polyethylene (average MW about 21,000) and paraffin liquid) or ESMA-P™ (a microcrystalline wax). It is, however, generally preferred to select an ointment or lotion base excipient which, on application, imparts to skin, hair and scalp a less oily appearance than does liquid paraffin, such as for instance heptamethylnonane.

As an example, preparation of a composition according to the invention is typically performed by melting the base excipient (e.g. heptamethyinonane and/or hydrogenated castor oil), adding a solution (typically at a concentration in the range of 0.0005–2.5% w/w) of the vitamin D analogue in the required amount of solvent, e.g. Arlamol® E, followed by addition of a dispersion of the corticosteroid in base excipient, typically with a particle size of from 0.1 to 20 µm, and then cooling the mixture. Typical content ranges of the various components in the finished composition according to the invention are from about 0.005 to about 0.3% w/w, preferably 0.01–0.2% w/w, of the corticosteroid, from about 0.0001 to about 0.035% w/w of the vitamin D analogue, from about 0.1 to about 25/5% w/w, preferably about 0.5–10% w/w, of the viscosity-increasing agent, optionally from about 0.5 to about 10% w/w of the surfactant, and from about 1 to about 30% w/w of the solvent, the remainder typically being primarily base excipient such as the above-mentioned heptamethylnonane. The composition may also contain other commonly used additives such as antioxidants (e.g. α-tocopherol).

In a particular embodiment intended for application on the scalp, the present composition may additionally comprise a surfactant. This may be an advantage in cases where it is intended to apply the composition and leave it on the scalp for a sufficient period of time to ensure that the active components are absorbed in the skin of the scalp after which the remainder of the composition may be washed away to give the hair a "clean" (non-oily) appearance. The surfactant may be selected from fatty esters of a type generally considered suitable for application on the scalp, e.g. sorbitan monolaurate, sorbitan monopalmitate, sorbitan monostearate, sorbitan monooleate, polyoxyethylene sorbitan monolaurate, polyoxyethylene sorbitan monopalmitate, polyoxyethylene sorbitan monostearate or polyoxyethylene sorbitan monooleate. However, some vitamin D analogues tend to be degraded in the presence of even small amounts of free fatty acids found as impurities in esters. Preferred surfactants for inclusion in compositions comprising such vitamin D analogues are therefore ethers, e.g. ethers selected from the group consisting of octoxynol-n of formula $C_8H_{17}C_6H_4(OCH_2CH_2)_nOH$, wherein n is an integer of from 1 to 70, nonoxynol-n of formula $C_9H_{19}C_6H_4$ (OCH$_2$CH$_2$)$_p$OH, wherein p is an integer of from 4 to 40, and a polyoxyethylene C$_{12-22}$ alkyl ether, e.g. polyoxyethylene lauryl ether, polyoxyethylene cetyl ether, polyoxyethylene stearyl ether or polyoxyethylene oleyl ether.

The resulting composition may conveniently be filled into an appropriate container, e.g. a metal or plastic tube, a bottle, or a dispenser provided with suitable means to measure a correct dose of the composition.

The composition of the invention may further comprise an anti-fungal agent which is, e.g., selected from the group consisting of miconazol, clotrimazol, terbinafin, ciclopirox, bifonazol, nystatin, ketoconazol, econazol, and fluconazol.

Preferably, the compositions according to the invention do not contain therapeutically effective compounds selected from the group consisting of the xanthine derivatives pentoxifylline, propentofyllin, and torbafylline, or any other xanthine or xanthine derivative.

The invention also relates to a method of treatment of psoriasis and related skin diseases, e.g. sebo-psoriasis of the scalp, comprising topically administering an effective amount of a composition according to the invention to a patient in need of such treatment. Said method preferably comprises topical administration once or twice a day of a therapeutically sufficient dosage of said composition. The composition according to the invention preferably contains about 0.001–0.5 mg/g or ml, preferably about 0.001–0.25 mg/g or ml, of the vitamin D or vitamin D analogue, and about 0.05–2 mg/g or ml, preferably about 0.1–1.5 mg/g or ml, of the corticosteroid.

The invention is further illustrated by the following examples which are not in any way intended to limit the scope of the invention as claimed.

EXAMPLE 1

Gel Formulation Containing Calcipotriol and Betamethasone

To produce 1 kg of gel formulation, 30 g of hydrogenated castor oil was melted together with 749 g of heptamethylnonane at 85–90° C. and cooled with homogenisation to about 60° C. The mixture was then cooled to 25–30° C. with stirring. 643 mg of betamethasone dipropionate was suspended in 50 g of heptamethylnonane and added to the homogenised gel base. 52.2 mg of calcipotriol hydrate or 50 mg of calcipotriol was dissolved in 170 g polyoxypropylene-15-stearyl ether and added to the mixture of the other ingredients, and the formulation was homogenised to ensure a homogenous distribution of the active components. The resulting gel formulation was stable when stored at 40° C. for 3 months, indicating a shelf life of at least 2 years at room temperature. The stability figures are shown in the tables 1 and 2 below.

TABLE 1

| Start 5°C./1 month | | 40° C. 1 month | | 40° C. 3 months | |
|---|---|---|---|---|---|
| BDP % FOS | Calcipotri. % FOS | BDP % FOS | Calcipotri. % FOS | BDP % FOS | Calcipotri. % FOS |
| 0.23 | 1.59 | 0.91 | 1.52 | 1.02 | 1.33 |
| BDP Kvant. | Calcipotri. Kvant. | BDP Kvant. | Calcipotri. Kvant. | BDP Kvant. | Calcipotri. Kvant. |
| 0.634 | 50.16 | 0.642 | 50.0 | | |

TABLE 2

| Start 5°C./1 month | | 40° C. 1 month | | 40° C. 3 months | |
|---|---|---|---|---|---|
| BDP % FOS | Calcipotri. % Epi | BDP % FOS | Calcipotri. % Epi | BDP % FOS | Calcipotri. % Epi |
| 0.23 | 0.62 | 0.91 | 0.66 | 1.02 | 0.8 |

1 g of the lotion contains:

| | |
|---|---|
| betamethasone (as dipropionate: 0.643 mg) | 0.5 mg |
| calcipotriol (as hydrate: 52.2 μg) | 50 μg |
| polyoxypropylene-15-stearyl ether (Arlamol ® E) | 170 mg |
| hydrogenated castor oil | 30 mg |
| heptanethylnonane (Arlamol ® HD) to make | 1 g |

What is claimed is:

1. A substantially non-aqueous pharmaceutical gel composition for application on skin, said composition comprising at least one vitamin D analogue selected from the group consisting of seocalcitol; calcipotriol; hydrate of calcipotriol; calcitriol; tacalcitol, maxacalcitol; paricalcitol; falecalcitriol; 1α, 24S-dihydroxy-vitamin D2; and 1(S),3(R)-dihydroxy-20(R)-[((3-(2-hydroxy-2-propyl)-phenyl)-methoxy)-methyl]-9,10-secopregna-5 (Z),7(E),10(19)-triene and mixtures thereof, at least one corticosteroid, a viscosity-increasing excipient in an amount resulting in a viscosity in the range of from about 5 mPa.s to about 500 mPa.s, and at least one solvent selected from the group consisting of:
(i) compounds of the general formula R$^3$(OCH$_2$C(R$^1$) H)$_x$OR$^2$ (I) wherein x is in the range of 2–60, R$^1$ in each of the x units independently is H or CH$_3$, R$^2$ is straight chain or branched C$_{1-20}$alkyl or benzoyl, and R$^3$ is H or phenylcarbonyloxy;
(ii) di-(straight or branched)-C$_{4-10}$ alkyl esters of C$_{4-C8}$ dicarboxylic acids;
(iii) straight or branched C$_{12-18}$-alkyl benzoates;
(iv) straight or branched C$_{2-4}$-alkyl esters of straight or branched C$_{10-18}$-alkanoic or -alkenoic acids;
(v) propylenglycol diesters with C$_{8-14}$-alkanoic acids; and
(vi) branched primary C$_{18-24}$ alkanols, said composition being stable when stored at 40° C. for 3 months.

2. The composition according to claim 1, which has a viscosity in the range of from about 10 mPa.s to about 250 mPa.s.

3. The composition according to claim 1, wherein the viscosity-increasing excipient is a thixotropic gelling agent.

4. The composition according to claim 3, wherein the thixotropic gelling agent is hydrogenated castor oil.

5. The composition according to claim 1, wherein said composition comprises a viscosity-increasing excipient which is a wax, polyethylene or a microcrystalline wax.

6. The composition according to claim 1, wherein said solvent is selected from compounds of the general formula H(OCH$_2$C(R$^1$)H)$_x$OR$^2$ (I) wherein R$^1$, x, and R$^2$ are as defined in claim 1 and mixtures thereof.

7. The composition according to claim 1, wherein R$^1$ is CH$_3$.

8. The composition according to claim 6, wherein said solvent is polyoxypropylene-15-stearyl ether.

9. The composition according to claim 1, wherein said vitamin D analogue is selected from the group consisting of calcipotriol; calcitriol; tacalcitol, maxacalcitol; 1(S),3(R)-dihydroxy-20(R)-[((3-(2-hydroxy-2-propyl)-phenyl)-methoxy)-methyl]-9,10-seco-pregna-5(Z),7(E),10(19)-triene, as well as mixtures thereof, 10. The composition according to claim 1, wherein the vitamin D analogue is effective against psoriasis and sebo-psoriasis of the scalp in humans.

11. The composition according to claim 1, wherein said vitamin D analogue is calcipotriol or its hydrate.

12. The composition according to claim 1, wherein said corticosteroid is selected from the group consisting of Betamethasone, Clobetasol, Clobetasone, Desoximethasone, Diflucortolon, Diflorasone, Fluocinonid, Flumethasone, Fluocinolon, Fluticasone, Fluprednidene, Halcinonide, Hydrocortisone, Mometasone, Triamcinolon, Pharmaceutically acceptable esters thereof, acetonides thereof and mixtures thereof.

13. The composition according to claim 12, wherein said esters or acetonides are selected from the group consisting of 17-valerate, 17-propionate, 17,21-dipropionate acetonide, acetonide-21N-benzoyl-2-methyl-β-alaninate, acetonide-21-(3,3-dimethylbutyrate) and 17-butyrate.

14. The composition according to claim 1, wherein said composition contains 0.001–0.25 mg/g or ml of said vitamin D analogue and 0.05–2 mg/g or ml of said corticosteroid.

15. The composition according to claim 1, wherein said composition comprises the following ingredients (per g of the composition):

betamethasone (as dipropionate: 0.643 mg) 0.5 mg calcipotriol (as hydrate: 52.2 μg) 50 μg polyoxypropylene-15-stearyl ether 170 mg hydrogenated castor oil 30 mg heptamethylnonane to make 1 g.

16. The composition according to claim 1, which further comprises an antifungal agent.

17. The composition according to claim 1 for application on the scalp.

18. The composition according to claim 17, additionally comprising a surfactant.

19. The composition according to claim 18, wherein the surfactant is selected from the group consisting of octoxynol-n of formula $C_8H_{17}C_6H_4(OCH_2CH_2)_nOH$, wherein n is an integer of from 1 to 70, nonoxynol-n of formula $C_9H_{19}C_6H_4(OCH_2CH_2)_pOH$, wherein p is an integer of from 4 to 40, and a polyoxyethylene $C_{12\text{-}22}$ alkyl ether.

20. A method of treating psoriasis or sebo-psoriasis of the scalp, the method comprising administering to an affected skin area of a patient in need thereof an effective amount of the composition according to claim 1.

21. The method of claim 20, wherein said composition is administered once or twice a day.

22. The method of claim 20, wherein said composition is administered to the scalp.

23. The method of claim 20, wherein said composition is administered once a day.

* * * * *

UNITED STATES PATENT AND TRADEMARK OFFICE
CERTIFICATE OF CORRECTION

PATENT NO. : 6,787,529 B2 Page 1 of 1
APPLICATION NO. : 09/984072
DATED : September 7, 2004
INVENTOR(S) : Gert Hoy et al.

It is certified that error appears in the above-identified patent and that said Letters Patent is hereby corrected as shown below:

On Title page: Item (*) Notice, should read,

Item (*), Notice, add the following paragraph:

Subject to any disclaimer, the term of this patent is extended or adjusted under 35 U.S.C. 154(b) by 0 days.

--This patent is subject to a terminal disclaimer. --

Signed and Sealed this

Third Day of July, 2007

JON W. DUDAS
*Director of the United States Patent and Trademark Office*